United States Patent
Sinha et al.

(10) Patent No.: US 11,573,205 B2
(45) Date of Patent: Feb. 7, 2023

(54) MULTIMODAL CHARACTERIZATION OF A FLUID USING A SINGLE DROPLET

(71) Applicant: AWE Technologies, LLC, Bay Shore, NY (US)

(72) Inventors: Dipen N. Sinha, Bay Shore, NY (US); Peter G. Espina, Bay Shore, NY (US)

(73) Assignee: AWE Technologies LLC, Bay Shore, NY (US)

( * ) Notice: Subject to any disclaimer, the term of this patent is extended or adjusted under 35 U.S.C. 154(b) by 409 days.

(21) Appl. No.: 16/843,669

(22) Filed: Apr. 8, 2020

(65) Prior Publication Data

US 2020/0326312 A1 Oct. 15, 2020

Related U.S. Application Data

(60) Provisional application No. 62/833,467, filed on Apr. 12, 2019.

(51) Int. Cl.
| | |
|---|---|
| *G01N 29/036* | (2006.01) |
| *G01N 33/52* | (2006.01) |
| *G01N 29/22* | (2006.01) |
| *G01N 29/24* | (2006.01) |
| *G01N 33/49* | (2006.01) |
| *G01N 29/34* | (2006.01) |

(Continued)

(52) U.S. Cl.
CPC ......... *G01N 29/036* (2013.01); *G01N 29/022* (2013.01); *G01N 29/028* (2013.01); *G01N 29/222* (2013.01); *G01N 29/2443* (2013.01); *G01N 29/348* (2013.01); *G01N 33/49* (2013.01); *G01N 33/52* (2013.01); *G01N 2015/1481* (2013.01); *G01N 2291/02466* (2013.01)

(58) Field of Classification Search
CPC .. G01N 29/036; G01N 29/022; G01N 29/028; G01N 29/222; G01N 29/2443; G01N 29/348; G01N 29/24; G01N 29/34; G01N 29/221; G01N 33/52; G01N 33/49
See application file for complete search history.

(56) References Cited

U.S. PATENT DOCUMENTS

| | | | |
|---|---|---|---|
| 5,739,432 A * | 4/1998 | Sinha ................... | G01N 29/036 73/61.79 |
| 5,811,682 A | 9/1998 | Ohtani et al. | |

(Continued)

OTHER PUBLICATIONS

The International Search Report and Written Opinion of the International Searching Authority, PCT/US2020/27396, dated Jul. 17, 2020, 13 pages.

*Primary Examiner* — Helen C Kwok
(74) *Attorney, Agent, or Firm* — Samuel M. Freund; Cochran Freund & Young LLC (57) ABSTRACT

Apparatus for performing multiple different measurements on a small specimen sample, enabling testing and diagnoses in real time at the point of care are described. The core of the apparatus includes an ultrasonic resonator cavity where acoustic resonances are used to determine the speed of sound and sound attenuation in a single droplet. Acoustic measurements are made in the reflection mode using electrical impedance of a small piezoelectric crystal transducer that operates in the thickness longitudinal mode. Combination of this technology with electromagnetic, electrical, and magnetic fields permits multiple types of measurements to be made using the same resonator cavity.

21 Claims, 8 Drawing Sheets

(51) Int. Cl.
*G01N 29/028* (2006.01)
*G01N 29/02* (2006.01)
*G01N 15/14* (2006.01)

(56) References Cited

U.S. PATENT DOCUMENTS

| | | | |
|---|---|---|---|
| 5,886,262 A | | 3/1999 | Sinha |
| 6,832,506 B1 * | | 12/2004 | Mason .................. G01N 29/02 73/590 |
| 7,819,006 B2 * | | 10/2010 | Brooks .................. A61B 5/05 600/15 |
| 2011/0188337 A1 | | 8/2011 | Rathgeber et al. |
| 2017/0321177 A1 | | 11/2017 | Weitz et al. |
| 2018/0095067 A1 * | | 4/2018 | Huff ................ G01N 33/48721 |

* cited by examiner

MULTIMODAL CHARACTERIZATION OF A FLUID USING A SINGLE DROPLET

CROSS-REFERENCE TO RELATED APPLICATIONS

The present application claims the benefit of U.S. Provisional Patent Application No. 62/833,467 for "Multimodal Characterization Of A Fluid Using A Single Droplet" by Dipen N. Sinha and Peter G. Espina, which was filed on 12 Apr. 2019, the entire contents of which patent application is hereby specifically incorporated by reference herein for all that it discloses and teaches.

BACKGROUND

There are few techniques for analysis and characterization of physical properties of fluids when there are only a few microliters or less of available fluid. Bodily fluids available only in small quantities include blood, tear drops, sweat, saliva, and sputum, as examples. Urine is usually available in larger quantities, but it is desirable to use only small samples, if possible. Measurements on such fluids are either optical or chemically based.

Blood samples are generally analyzed using multiple techniques, biochemical analysis, molecular profiles, and cellular evaluations, being examples. For each type of analysis, a different sample of fluid from the same subject is used as these are performed in a parallel manner using different instruments. For full blood counts or analysis of bacterial growth, optical microscopy is the standard procedure. Other medical diagnostic testing using saliva, as an example, is not common except for DNA extraction.

SUMMARY

In accordance with the purposes of the present invention, as embodied and broadly described herein, an embodiment of the apparatus for optically and ultrasonically characterizing a single droplet of a liquid, hereof, includes: a piezoelectric crystal effective for operating in the thickness longitudinal mode, and having an electrical impedance responsive to acoustic waves impinging thereon; a metal holder having a front surface having a cavity adapted to receive and hold the piezoelectric crystal in electrical contact with the metal holder; a flat, optically transparent substrate having a first surface and a second surface, the first surface being disposed parallel to and a chosen distance from the front surface of the metal holder, forming thereby an acoustic resonance cavity within which the single droplet is held by surface tension forces; a source of optical radiation for directing optical radiation onto the second surface of the substrate, through the first surface of the substrate, and into the droplet; an acoustic function generator for sweeping the piezoelectric crystal through a chosen frequency range, whereby a series of resonances, equally spaced in frequency, is generated in the liquid drop; an impedance analyzer for measuring the impedance of the piezoelectric crystal as a function of frequency; and a signal processor for receiving the output from the impedance analyzer and for determining the spacing between equally spaced resonances, from which speed of sound and sound attenuation in the liquid drop are determined.

In accordance with the purposes of the present invention, as embodied and broadly described herein, an embodiment of the apparatus for electrically and ultrasonically characterizing a single droplet of a liquid, hereof, includes: a piezoelectric crystal effective for operating in the thickness longitudinal mode, and having an electrical impedance responsive to acoustic waves impinging thereon; a metal holder having a front surface having a cavity adapted to receive and hold the piezoelectric crystal in electrical contact with the metal holder; a flat substrate having a first surface and a second surface, the first surface being disposed parallel to and a chosen distance from the front surface of the metal holder, forming thereby an acoustic resonance cavity within which said single droplet is held by surface tension forces, the first surface further having parallel or concentric electrically conducting portions thereon; an acoustic function generator for sweeping the piezoelectric crystal through a chosen frequency range, whereby a series of resonances, equally spaced in frequency, is generated in the liquid drop; an electric power supply for providing an electric field between the electrically conducting portions; an impedance analyzer for measuring the impedance of the piezoelectric crystal as a function of frequency; and a signal processor for receiving the output from the impedance analyzer and for determining the spacing between equally spaced resonances, from which speed of sound and sound attenuation in the liquid drop are determined.

In accordance with the purposes of the present invention, as embodied and broadly described herein, an embodiment of the apparatus for magnetically and ultrasonically characterizing a single droplet of a liquid, hereof, includes: a piezoelectric crystal effective for operating in the thickness longitudinal mode, and having an electrical impedance responsive to acoustic waves impinging thereon; a metal holder having a front surface having a cavity adapted to receive and hold the piezoelectric crystal in electrical contact with the metal holder; a flat substrate having a first surface and a second surface, the first surface being disposed parallel to and a chosen distance from the front surface of the metal holder, forming thereby an acoustic resonance cavity within which the single droplet is held by surface tension forces; an acoustic function generator for sweeping the piezoelectric crystal through a chosen frequency range, whereby a series of resonances, equally spaced in frequency, is generated in the liquid drop; two flat, parallel, spaced-apart coils, one of the two coils disposed on or in the vicinity of each of the first surface and the second surface of the substrate, and parallel thereto, each of the coils having an axis collinear with the axis of the other of the coils; a current source for providing electric current to each of the coils such that a uniform magnetic field perpendicular to the first surface and the second surface of the substrate is generated in the same direction by each coil; an impedance analyzer for measuring the impedance of the piezoelectric crystal as a function of frequency; and a signal processor for receiving the output from the impedance analyzer and for determining the spacing between equally spaced resonances, from which speed of sound and sound attenuation in the liquid drop are determined.

In accordance with the purposes of the present invention, as embodied and broadly described herein, an embodiment of the apparatus for electromagnetically and ultrasonically characterizing a single droplet of a liquid, hereof, includes: a piezoelectric crystal effective for operating in the thickness longitudinal mode, and having an electrical impedance responsive to acoustic waves impinging thereon; a metal holder having a front surface having a cavity adapted to receive and hold the piezoelectric crystal in electrical contact with the metal holder; a flat substrate having a first surface and a second surface, the first surface being disposed parallel to and a chosen distance from the front surface of the metal holder, forming thereby an acoustic resonance cavity within which the single droplet is held by surface tension forces; an acoustic function generator for sweeping the piezoelectric crystal through a chosen frequency range, whereby a series of resonances, equally spaced in frequency, is generated in the liquid drop; a source of mm-wave electromagnetic radiation, the electromagnetic radiation impinging on said single droplet; an electric power supply for providing power to the source of mm-wave electromagnetic radiation; an impedance analyzer for measuring the impedance of the piezoelectric crystal as a function of frequency; and a signal processor for receiving the output from the impedance analyzer and for determining the spacing between equally spaced resonances, from which speed of sound and sound attenuation in the liquid drop are determined.

Benefits and advantages of the present invention include, but are not limited to, apparatus for performing multiple different measurements on a small, droplet sized, specimen sample, which may include fecal material, enabling testing and diagnoses in real time at the point of care.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 5A, is a schematic representation of a perspective view of an embodiment of an apparatus where an electric field is combined with acoustic measurements, utilizing an apparatus similar to that of FIG. 3, hereof, except that electrodes are formed on or attached to the surface of the substrate, and powered by an ac power supply; and schematic representations of top views of two embodiments of interdigitated electrodes shown in FIGS. 5B and 5C, respectively, can also be used if higher field strengths are required.

FIG. 8A is a schematic representation of a side view of an embodiment of an apparatus where a magnetic field is combined with acoustic measurements, illustrating a uniform magnetic field, either DC or pulsed, generated by placing two flat coils on opposite sides of the substrate, while

DETAILED DESCRIPTION OF THE INVENTION

Briefly, embodiments of the present process include apparatus for performing multiple different measurements on a small specimen sample, enabling testing and diagnoses in real time at the point of care. The core of the apparatus includes an ultrasonic resonator cavity where acoustic resonances are used to determine the speed of sound in a single droplet. Acoustic measurements are made in the reflection mode using the electrical impedance of a small piezoelectric crystal transducer that operates in the thickness longitudinal mode. Combination of this technology with optical, electrical, and magnetic apparatus permits multiple types of measurements to be made.

Figure 1:
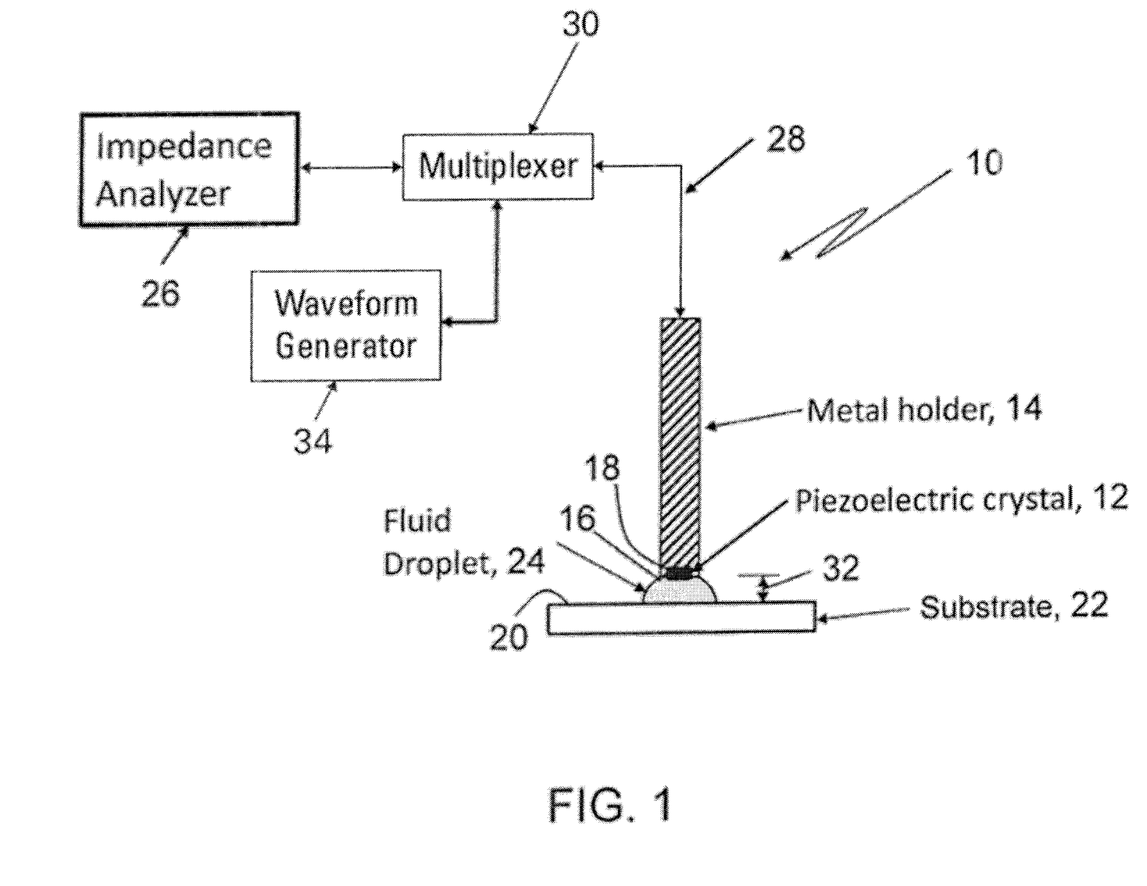
FIG. 1 is a schematic representation of a side view of an embodiment of the apparatus for determining the speed of sound in a single droplet of liquid using reflection mode swept frequency acoustic interferometry (SFAI).

Reference will now be made in detail to the present embodiments of the invention, examples of which are illustrated in the accompanying drawings. In the Figures, similar structure will be identified using identical reference characters. It will be understood that the FIGURES are presented for the purpose of describing particular embodiments of the invention and are not intended to limit the invention thereto. Turning now to FIG. 1, a schematic representation of a side view of a generalized embodiment of apparatus, 10, for determining the speed of sound and attenuation in a single droplet, using reflective swept frequency acoustic interferometry (SFAI), is illustrated. This measurement provides the basic measurement for the combined optical/acoustic, electrical/acoustic, and magnetic/acoustic measurement combinations described below.

Acoustic measurements are made in the reflection mode by measuring the electrical impedance of single, 0.5 mm diameter piezoelectric crystal, 12, operating in the thickness, longitudinal mode, and having a frequency range between 5 MHz and 20 MHz. A 20 MHz piezoelectric crystal is thin and fragile and physical support is necessary both for mechanical stability and for bandwidth enhancement by mechanically loading the back face of the crystal. Otherwise, the crystal will resonate within a very narrow bandwidth, and a broader bandwidth is necessary.

Because the surface area of piezoelectric crystal 12 is small, the resulting generated signal is likewise small. Therefore, the signal must be protected from external electrical pickup. Metal housing, 14, serves as an electrical shield (Faraday Cage) and also as a holder for handling the piezoelectric crystal. Generally, a microminiature co-axial cable is electrically connected to the piezoelectric crystal for further reducing the noise pickup. The long metal tube, as shown, is for convenience.

Piezoelectric crystal 12 occupies a portion of front surface 16 of holder 14. The piezoelectric crystal may be embedded in an epoxy material supported by a housing, such as metal housing 14. Clearly, other housings and crystal mounting arrangements can be envisioned. Because of its small size, piezoelectric crystal 12 behaves as a point source over the frequency region employed. This tends to broaden the acoustic beam and produce some edge effects. Therefore, front surface 16 of holder 14, being larger than the crystal embedded therein creates a better resonator cavity. Technically, it is possible to use the crystal face by itself without any extra material around it; however, commercial crystals are sold in holders for mechanical stability.

Piezoelectric crystal holder 14 is vertically supported in the vicinity of top surface, 20, of flat substrate, 22. It can also be oriented at an angle to substrate 22, or be supported beneath the substrate, if desired. Liquid drop, 24, (sub-microliters of fluid are all that is required) is first placed on surface 20 of substrate 22, and then crystal holder 14 is positioned over liquid drop 24 using a simple mechanical loading device (not shown in FIG. 1), where it is held by surface tension forces. Since the droplet is free-standing, no container is required, making sample preparation much simpler.

Impedance Analyzer, 26, which may include a return loss bridge and a matching network (combination of a parallel capacitor and resistor) that is used to balance the bridge, is connected to piezoelectric crystal 12 through a miniature co-axial cable, 28 (not detailed in FIG. 1), through multiplexer, 30. Commercial instruments, such as the Bode 100 system from Omicron, can measure electrical impedance of piezoelectric crystal 12 over a frequency range between a few Hz and 50 MHz. A Vector Network Analyzer version provides real and imaginary impedance values as a function of frequency, which provide amplitude and phase information. Such instruments provide a tracking band-pass filter function, as well as selectable filter bandwidth, important for reducing electrical noise pickup.

Substrate 22 can be of any material, but chemically stable materials having low optical absorbance may be selected as advantageous. The small sub-mm space, 32, between the piezoelectric crystal face, or front surface 16 of holder 14, and substrate 22 forms a resonator cavity. A variable sine-wave excitation frequency is applied to piezoelectric crystal 12 from waveform generator, 34, through multiplexer 30, generating longitudinal waves from the piezoelectric crystal that propagate between the piezoelectric crystal and the substrate. The frequencies at which standing waves are produced in the droplet (resonance frequencies) are related to the properties of the liquid (speed of sound) and the spacing between the piezoelectric crystal and the substrate. Each time the frequency is such that an integral number of the corresponding wavelength in the fluid equals the pathlength in the fluid, a resonance condition is set up. This resonance affects the electrical impedance of the crystal and is detected by the impedance analyzer.

FIGS. 2A-2D show the data obtained using a small, broadband piezoelectric crystal as illustrated in the apparatus of FIG. 1 with water as the fluid between substrate 22 and piezoelectric crystal 12.

Figure 2A:
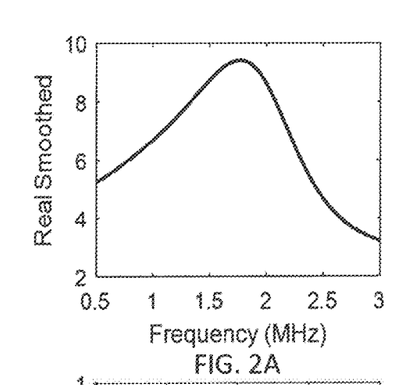
FIG. 2A is a graph of the frequency response of the real part of the electrical impedance of the piezoelectric crystal as a function of frequency when there is no liquid present.
Figure 2B:
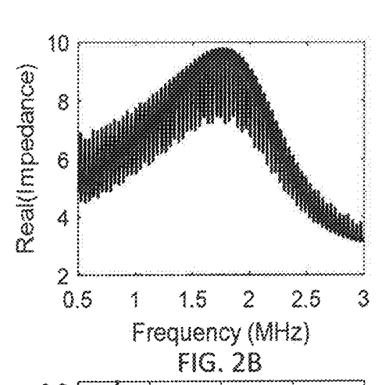
FIG. 2B is a graph of the frequency response of the real part of the electrical impedance of the piezoelectric crystal as a function of frequency there is a liquid (water) present between the crystal and the substrate, illustrating a periodic spectrum where each of the resonance line is equally spaced in frequency.

FIG. 2A is a graph of the frequency response of the real part of the electrical impedance of piezoelectric crystal 12 as a function of frequency when there is no liquid present. The impedance measured is a complex value that has both real and imaginary components (equivalent to measuring magnitude and phase). A periodic series of resonances, equally spaced in frequency, is shown in FIG. 2B when there is a liquid (water) is present between crystal 12 and substrate 22. The sound speed is given by the relationship:

$$\text{Sound speed} = 2 \times \text{liquid pathlength} \times \text{frequency spacing}.$$

Figure 2C:
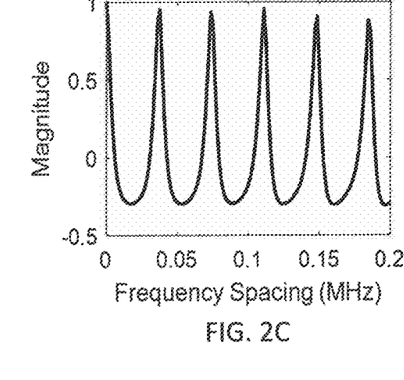
FIG. 2C is a graph of the auto-correlation amplitude as a function of the frequency spacing of the resonances shown in FIG. 2B, hereof after the baseline in FIG. 2B is subtracted.
Figure 2D:
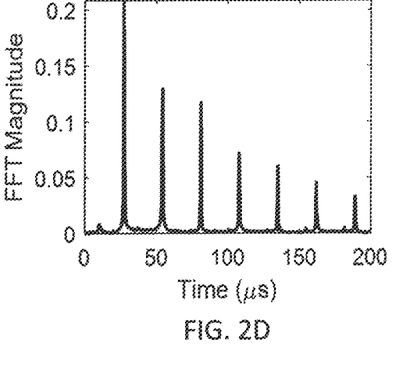
FIG. 2D is a graph of the magnitude of the Fast Fourier Transform of the data as a function of time, illustrating a series of equally spaced (in time) peaks that are exponentially decaying in amplitude.

There are two common procedures for determining this frequency spacing. The first is to take the autocorrelation of the spectrum as shown in FIG. 2B after subtracting the baseline from the spectrum. The result of the autocorrelation is shown in the graph of FIG. 2C, where the auto-correlation amplitude is plotted versus frequency spacing. The position of the first peak provides the information needed for calculating sound speed. Analysis of the reflection mode spectrum may also be achieved by performing a Fast Fourier Transform (FFT) of the data, which converts the measurement from a measurement in the frequency-domain to one in the time-domain. The FFT result is shown in FIG. 2D, where the FFT magnitude is plotted versus time in μs. FIG. 2D shows features not present in the autocorrelation plot, namely a series of equally spaced (in time) peaks that are exponentially decaying in amplitude. This plot is equivalent to a pulse bouncing back and forth between piezoelectric crystal 12 and substrate 22 through the liquid 24. Here, the first peak represents the propagation of the first pulse from the piezoelectric crystal to the substrate and back to the crystal. If the pathlength is known, the time measurement to the first peak provides the sound speed. The remaining peaks are subsequent echoes. Due to absorption of sound in the liquid, energy is lost and appears as an exponentially decaying amplitude for each echo, which provides a measure of the sound absorption from the same measurement. The same measurement can also be made directly in the time domain by sending a short timescale pulse (<1 μs), and observing the return echoes on a very fast digitizer. Unless a digitizer having a multi-GHZ sampling rate is used, the accuracy of the measurement will suffer. Moreover, the electrical noise from the entire bandwidth of the piezoelectric crystal will be recorded along with signal.

Typical commercial instruments do not provide either FFT or Autocorrelation features; therefore, these data manipulations are performed in a digital signal processor (DSP), or a microprocessor or by a laptop with appropriate software. The apparatus of FIG. 3 below, illustrates the use of this hardware.

Typically, because of the small size of the piezoelectric crystals employed, the actual signal is small, and amplification using a broadband amplifier and a large of number of averages need to be made to recover the echo signals shown in FIG. 2D. The process gain (gain=frequency bandwidth× duration of excitation) is small in the case of direct pulse measurements in the time domain where the excitation pulse is of the order of 1 μs or less. By contrast, a frequency sweep is typically performed over a timescale longer than 1 s, yielding a factor of about $10^6$ in the process gain (1 μs compared to 1 s). Additionally, at each frequency step in the frequency sweep measurement, the bandwidth of the measurement can be restricted to between 100 Hz and 1 kHz, which is equivalent to use of a tracking filter where a fixed narrow bandwidth bandpass filter follows each frequency measurement in the entire frequency sweep. If one assumes a 1 kHz bandwidth for each frequency step measurement in the frequency sweep over a bandwidth of 10 MHz, the signal-to-noise ratio gain is 10 MHz/1 kHz or a factor of $10^5$. Therefore, the frequency sweep approach plays a major role in detecting the small signals involved in the measurement.

Figure 3:
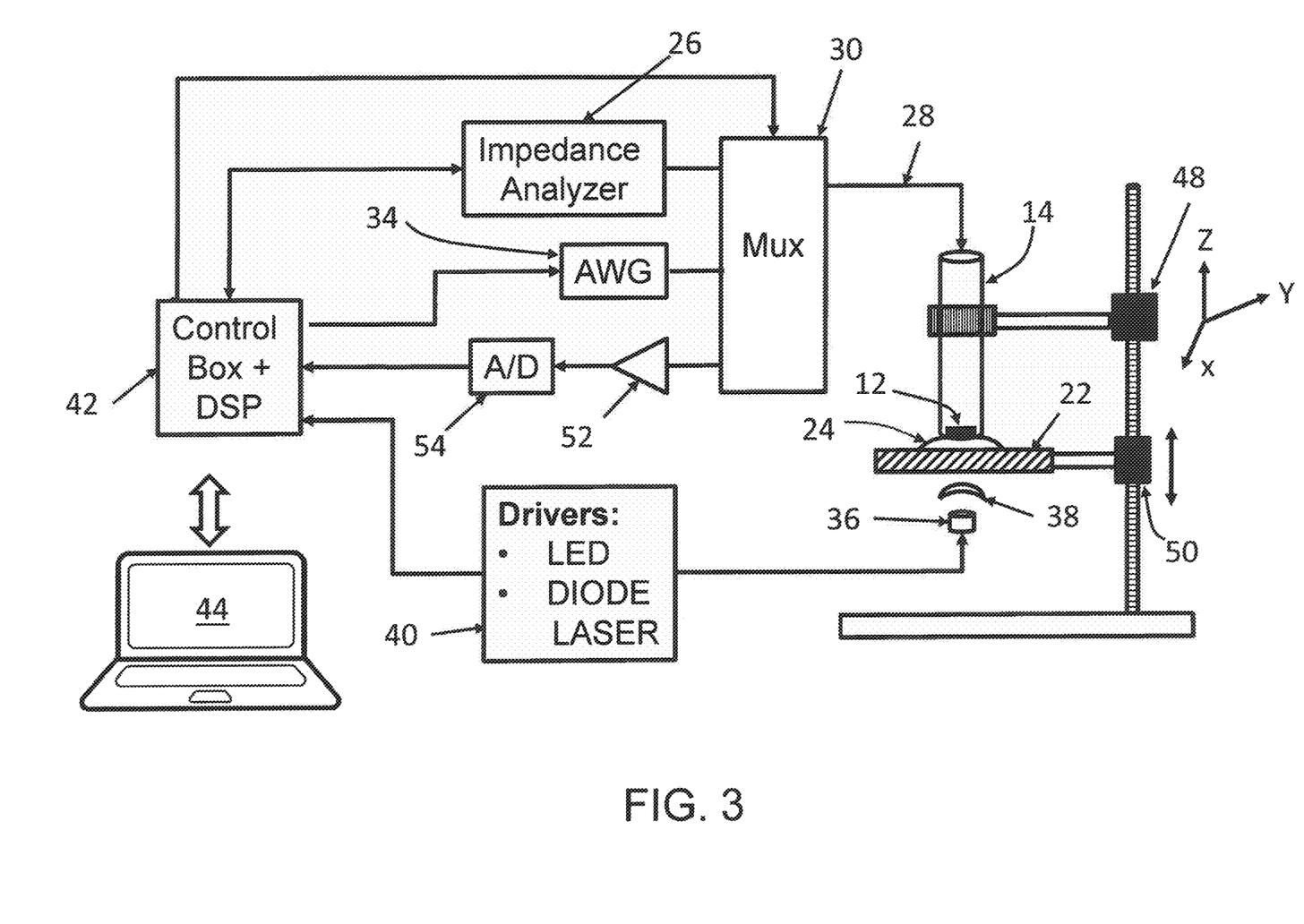
FIG. 3 is a schematic representation of a side view of an embodiment of an apparatus for measuring the effect of light absorption of certain species contained in a droplet specimen on the speed of sound in the droplet using reflection mode swept frequency acoustic interferometry, where the substrate comprises a material that is transparent over a broad light spectrum, and the fluid droplet specimen disposed above the substrate may be subjected to optical stimulation from below the substrate.

A. Combined Optical and Acoustic Measurements:

FIG. 3 shows the apparatus for measuring the effect of light absorption of certain species in a droplet specimen on the speed of sound in the droplet. If substrate 22 comprises a material that is transparent over a wide spectrum of light, fluid droplet specimen 24 disposed above the substrate can be subjected to optical stimulation from below the substrate. Examples of such substrates include, but are not limited to, Infrasil™ Quartz that has an effective range of 220 nm to 3800 nm. Infrared (IR) and near IR radiation penetrate most glass. The optical source, 36, may be a tunable diode laser or an high-power multi-wavelength LED, such as those available from LED Engin Inc., powered by driver, 40, controlled by digital signal processor and controller, 42, and processor, 44, which also provides data processing. One such LED source provides the following wavelengths, when driven at 700 mA current: Red (80-lumens), Green (140 lumens), Blue (33 lumens, White (210 lumens), Amber (70 lumens), Cyan (95 lumens), and Violet (0.90 W). Multiple LEDs may be combined to increase the optical power, if needed. Wavelengths can be individually selected and pulsed or some or all of the wavelengths may be combined together. Such an LED source can be used for excitation of any biological fluid containing various proteins and molecules, or any material that has absorption band in the excitation range. Lens, 38, may be employed to focus the light into droplet 24.

XY-positioning device, 48, permits holder 14 bearing piezoelectric crystal 12 to be accurately positioned over sample droplet 24, and Z-positioning device, 50, permits the distance 32 between front surface 16 of holder 14 and the top surface 20 of substrate 22 to be accurately chosen.

If any component of the fluid is selectively excited by certain wavelength, the absorbed energy will heat the fluid, which will alter the speed of sound therein. This change can be detected using a reflection mode acoustic measurement with a sensitivity of greater than 1 part per million in sound speed measurement. Selective excitation can therefore detect the presence of molecules or components of interest.

Figure 4:
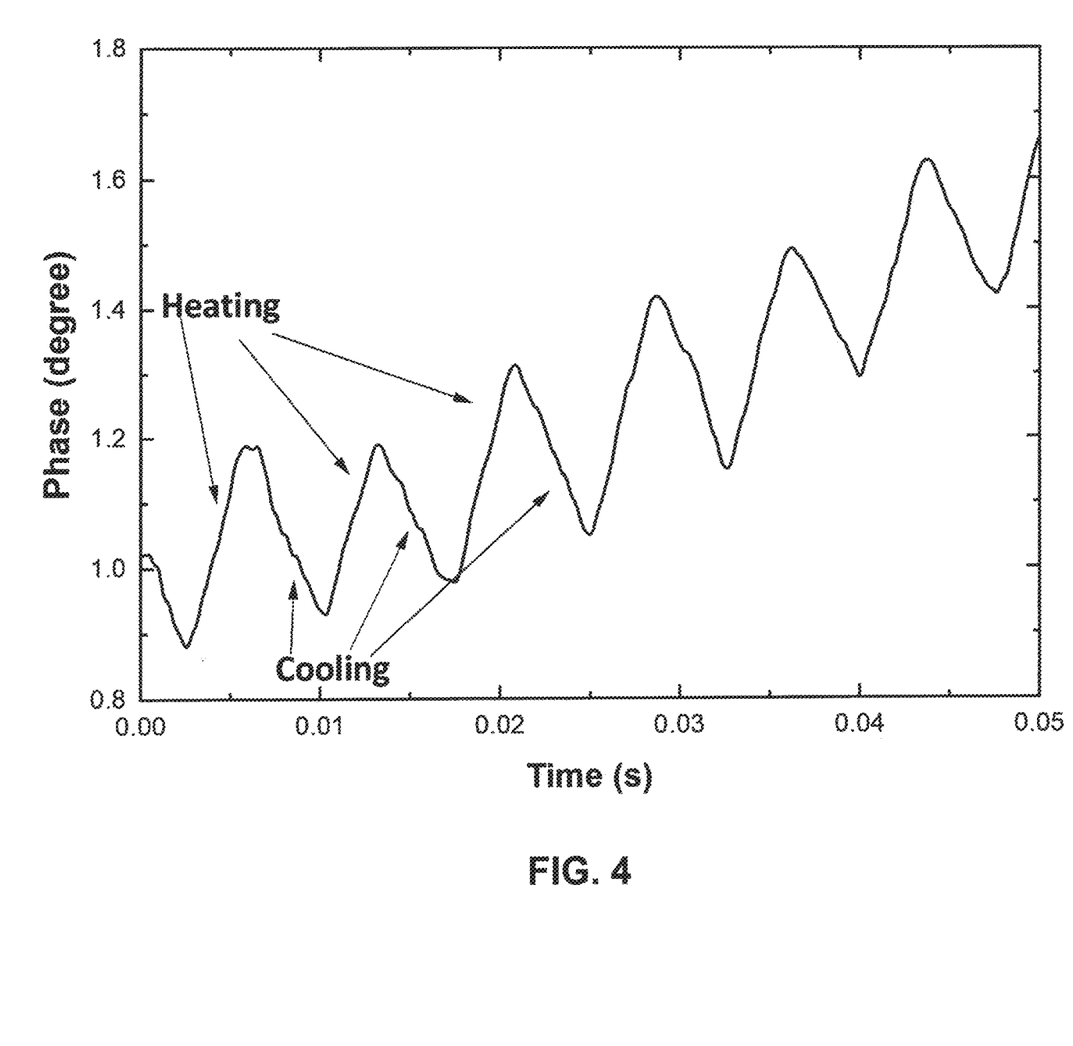
FIG. 4 is a graph of droplet heating and cooling as a function of time when a light source disposed below the substrate is pulsed on and off, the rate at which the liquid is heated being related to the thermal conductivity and diffusivity of the liquid.

FIG. 4 shows the result of a pulsed white light source turning on and off. When the light is on, the liquid (water) heats up and the sound speed changes and then cools down as the light is turned off. The rate at which the liquid heat is related to thermal conductivity and diffusivity if the liquid.

Light from the LED, or any other appropriate source, may also be excited by a short pulse of a chosen wavelength or a wavelength region, which gives rise to a photoacoustic measurement. An LED can be pulsed in the tens of picoseconds to tens of nanoseconds region by an electric current pulse from a pulse amplifier. The pulse is typically repeated at a constant rate of few kHz to several tens of kHz, which permits signal averaging and better signal quality in terms of signal-to-noise ratio. If the light is absorbed by the fluid or any of its internal components (e.g., biomolecules, proteins, bound antigens etc.), the liquid will undergo rapid heating, expand and produce a shock wave. This shock wave is a pressure pulse generated within the fluid droplet and bounces back and forth in the resonator cavity formed by piezoelectric crystal or the front surface of the holder, and the substrate. A resonance (standing wave) occurs in a cavity or in any system when an external excitation matches the time of an acoustic signal to bounce back and forth within the cavity. Once a photoacoustic signal is generated in the fluid due to light absorption, it travels in all directions. However, signals that travel in the direction normal to the two walls of the resonator cavity (the crystal face and the substrate) grow in intensity as the signal bounces back and forth many times before decaying. The Quality factor (Q-factor) is a measure of the cavity quality and sets the number of times a signal with bounce back and forth before completely decaying. However, the signal is reinforced each time it completes a cycle, then it does not decay but steadily increases in amplitude—it keeps building up at the same time as decaying, and the signal amplifies to a certain maximum value before there is an equilibrium. The Q-factor of the cavity can be as much as 100, which means that the signal can be amplified at least 100 times. Therefore, by timing the repetition rate of the LED pulse, one can take advantage of this mechanical cavity gain; that is, the repetition rate can be timed to any of the natural resonance vibrations of the substrate as well enhancing the small signal. The amplified small signal is then further amplified by amplifier, 52, and digitized by fast digitizer, 54, in FIG. 3. The pulse repetition rate of the LED can be synchronized in a manner that further amplification of the signal takes place. In this case of repeated pulsing and resonance, a much slower digitizer can be used to capture the signal, since the signal is built up from multiple samples.

This combination of optical and acoustic methods (photoacoustic measurement) can have parts per billion sensitivity.

For some acoustic measurements, better measurement accuracy on a sample may be obtained if the measurement is compared with that of a droplet of distilled water. Therefore, the apparatus of FIG. 3 may include the protocol of first performing measurements on a drop of distilled water disposed close to the sample droplet to be investigated, but not touching one another. First measurements, such as sound attenuation as a function of frequency, may be performed on the droplet of distilled water, followed by measurements on the test sample. Distilled water provides a known reference since both the water droplet and test sample are at the same temperature. In this manner excess attenuation may be measured as a function of frequency with greater resolution than making absolute measurements. All other measurements described in this disclosure would also benefit from having a reference medium.

Figures 5A, 5B, 5C:
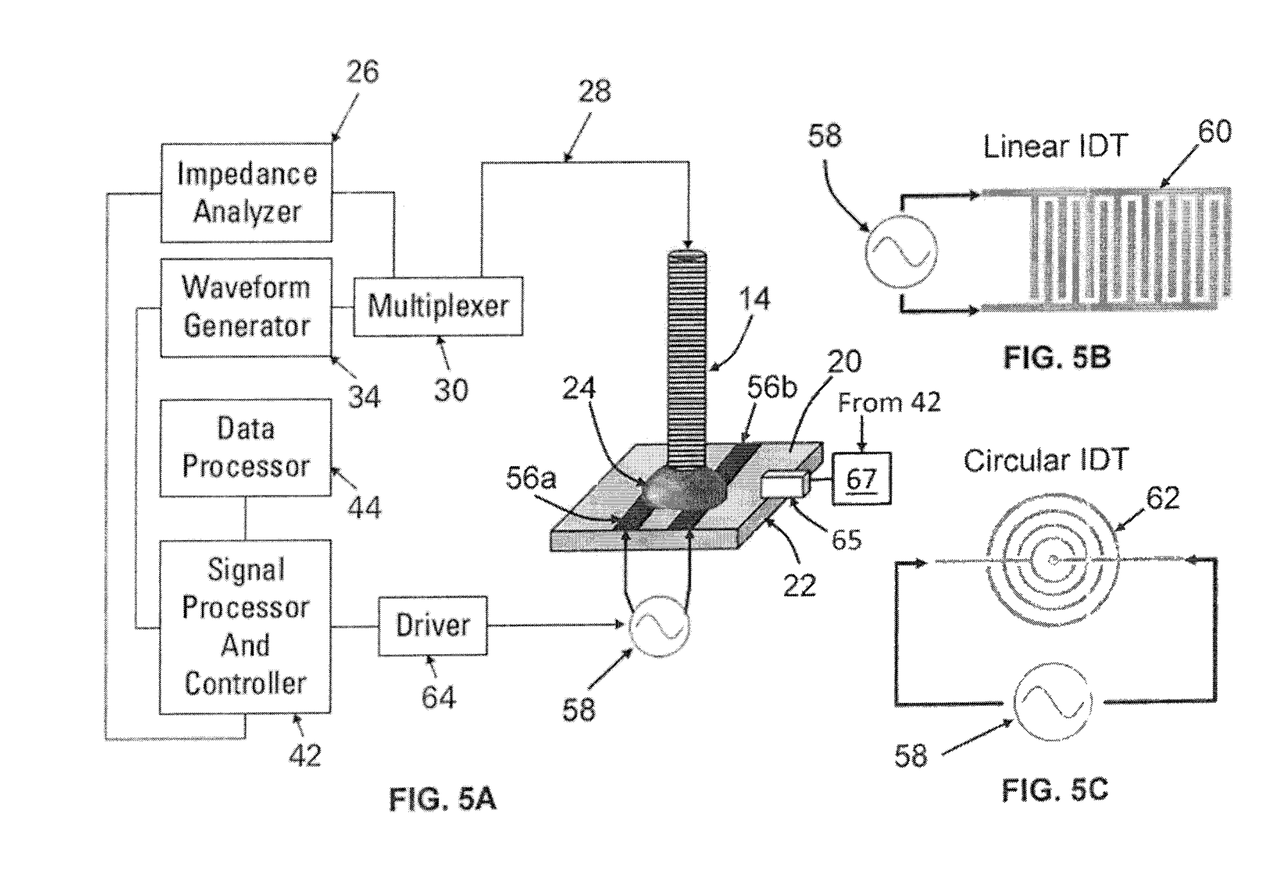

B. Combined Electrical and Acoustic Measurements:

(i) FIG. 5A illustrates a similar apparatus to that of FIG. 3 where an electric field is combined with acoustic measurements. Two spaced-apart, parallel electrical conductors or electrodes, 56a, 56b, are deposited on or attached to substrate 24, and powered using AC power supply, 58, for providing an alternating electric field to surface 20 of substrate 22. Droplet 24 and holder 14, bearing piezoelectric crystal 12 are shown disposed on or between conductors 56a and 56b. To be noted is that electrodes 56a and 56b behave as a capacitor; therefore, grounding of the open ends thereof is not required. It is the electric field generated between the electrodes that is important. Interdigitated electrodes (IDT), 60, and 62, shown in FIGS. 5B and 5C, respectively, can also be used if higher field strengths are needed. AC power supply 58 is controlled by driver 64 and controller 42. Except for driver 64 and AC power supply 58, the electronic controls and measurements are made using apparatus described in FIG. 3 above.

Electrodes 56a and 56b (and 60 and 62) can be made optically transparent. Materials such as Indium Tin Oxide (ITO), thin films of which are commonly deposited on surfaces by physical vapor deposition provide optically transparent electrodes. The parallel electrodes shown in FIG. 5A can also be formed as transmission lines that can be excited at frequencies as high as 20 GHz. Typically, three parallel lines are used, with the two outside lines being grounded, and the central conductor used as the signal line. Many macromolecules and protein structures are strongly affected by GHz electromagnetic waves, and energy may be absorbed from the transmission lines with the resulting effect being a change in the sound speed and ultrasonic absorption in the fluid at specific frequencies, in a similar manner to the ultrasonic measurements relating to light absorption, as discussed above.

Miniature millimeter-wave sources are now commercially available. Millimeter waves are electromagnetic waves defined to be between 30 and 300 GHz and correspond to wavelengths in air of 10 mm to 1 mm. As an example, high-speed wireless communications with the 802.11 Wi-Fi standard operates at 60 GHz. Mm-wave source, 65, powered by power supply, 67, controlled by digital signal processor and controller 42 and processor 44, is quite small and can be used to directly irradiate droplet 24, as shown in FIG. 5A. Such sources are available in various frequency ranges, and some may be tuned over a frequency range of several GHz. The electromagnetic energy may be passed through a small waveguide as part of mm-wave source 65. The higher frequency ranges interact well with biological cells, macromolecules, and protein structures. Many biological cells, including bacteria, decrease in size, and metabolism is altered, both of which will affect the acoustic properties of a droplet containing these cells.

Electrodes 56a and 56b (and 60 and 62) permit dielectrophoretic measurements to be made, and can induce microflow in the droplet sample. Dielectrophoresis (DEP) occurs from a force being exerted on a dielectric particle when subjected to a non-uniform electric field, and the DEP response of a cell is determined by its intrinsic dielectric property or, in broader terms, its electrical properties. This force does not require the particle to be charged, and all particles exhibit dielectrophoretic activity in the presence of electric fields.

The force depends on particle shape, size as well as the frequency of the electric field; consequently, fields having a particular frequency can manipulate particles with great selectivity. DEP can be used for separation of cells, such as red blood cells from white blood cells. Dielectric properties of a cell are associated with the physico-chemical properties of its plasma membrane and are an important consideration in terms of applying DEP to drug discovery. A potentially valuable application of DEP, then, is as a method to assess drugs aimed to induce changes of cell state, such as activation, apoptosis (a form of programmed cell death that occurs in multicellular organisms) and necrosis (caused by factors external to the cell or tissue, such as infection, toxins, or trauma, which result in the unregulated digestion of cell components). Thus, DEP is an electrokinetic technique capable of both selectively sorting cells and monitoring their physiological state, without the need for biomarkers such as fluorescent labels or antibody-coated magnetic beads. Further, the AC electrical fields and protocols typically used in DEP experiments are not known to damage the cells.

The combination of acoustic scattering with DEP therefor provides a powerful approach to sensitively and reliably determine these states of the cell and their interaction with drugs. That is, acoustic scattering is sensitive to the scatterer physical configuration and properties including shape. Thus, if the acoustic transducer is used as both transmitter and receiver as in a pulse-echo system and a frequency chirp (a short burst of linear swept frequency signal) signal is used, much information about the scatterer (e.g., blood cells or whatever one has) can be obtained. DEP, by contrast, separates solids from fluid and can develop a pattern of these on the substrate. The acoustic scattering from these well-defined patterns can then provide information about the system.

Because of the movement it can introduce in the fluid, the microscopic flow produced can enhance the growth of bacteria. This is called AC electrokinetic flow (ACEKF) for flow induced vortex in conducting solutions that improves immunoreaction efficiency. The electrode pattern can take many different shapes besides the ones shown in FIGS. 5A-5C.

Typically, bacteria growth rate is controlled by the type of bacteria and the nutrient medium, with growth slowing as the nutrients are depleted. Microflow can bring new nutrients into the vicinity of the bacteria, thereby enhancing the growth, which can be observed through sound speed measurements using the reflection mode acoustic measurements above the electrode. There are many such possibilities with a combination of acoustic and electric field. The small spacing of the electrodes in an IDT (either circular or linear) can generate very high field strength even with small voltages applied across the electrodes.

Figure 6:
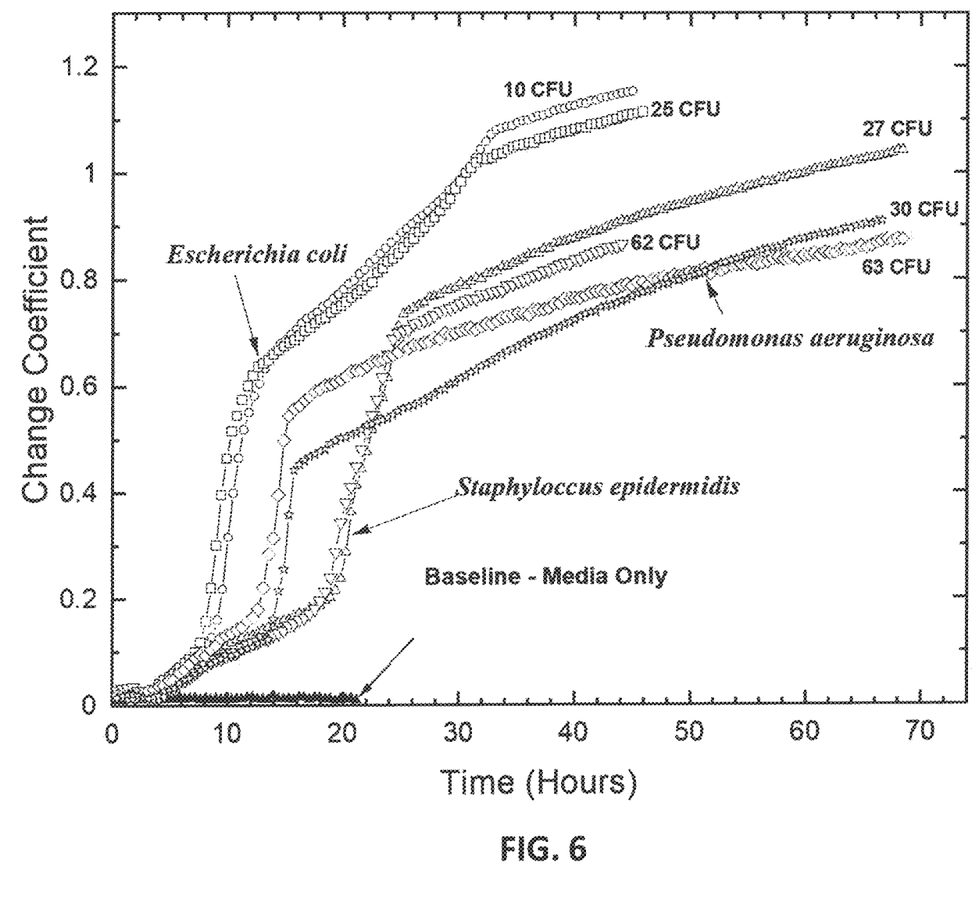
FIG. 6 illustrates graphs showing three types of bacteria growing in blood, with (a) being *Escherichia coli*, (b) being *Staphylococcus epidermis*, and (c) being *Pseudomonas aeruginosa*, where the change in slope indicates nutrient depletion at different stages of growth for the three different bacteria, with two different concentrations being studied for each type of bacteria using SFAI in a small spectrophotometric cell, one bacterium sample at a time.

FIG. 6 shows three types of bacteria growing in blood, with (a) being *Escherichia coli*, (b) being *Staphylococcus epidermis*, and (c) being *Pseudomonas aeruginosa*, where the change in slope indicates nutrient depletion at different stages of growth for the three different bacteria. Two different concentrations were studied for each type of bacteria using swept frequency acoustic interferometry (SFAI) in a small spectrophotometric cell, one bacterium sample at a time. The measurements were not taken using a single droplet, but such measurements can be done with the apparatus in FIGS. 5A-5C.

As the bacteria consume the nutrients around it, the sound speed of the surrounding fluid is affected. Bacterial growth can thus be measured through this sound speed variation using reflection mode SFAI. Each bacterial species observed had a different growth rate, which can be used as a signature to identify the bacterium assuming there is only one kind of bacteria.

Measurements were made under the following conditions. A temperature-controlled circulating bath was held at a nominal temperature of 37° C., the container for the bacteria was placed in the bath and slowly agitated. The signal processing was performed using a signal source (a digital function generator), a pair of acoustic transducers (one to transmit and one to receive), and a receiver (lock-in amplifier) phase-locked to the signal generator. The signal generator provided a sine wave output at 3.8 volts RMS, swept in frequency from 11 MHz to 16 MHz, to the transmitting acoustic transducer. The receiver, phase-locked to the signal source, received the signal from the transmitting transducer on the other side of the container and measured the phase and amplitude of the signal with respect to the reference. A standard desktop PC controlled the output of the signal source, in 200 Hz increments, and recorded the amplitude and phase data, as a function of frequency, from the receiver. In operation, the system makes baseline acoustic measurements of the growth media at the time of inoculation with each bacterium and at several minute increments over the duration of the test of several hours. The data shown in FIG. 6 illustrates the change in the acoustic properties of the growth media over time as the metabolic byproducts of bacterial growth accumulate in the media, and presents, when plotted, in the shape typical of bacterial growth curves.

The change in sound speed in the medium was derived from a cross-correlation method where the baseline spectrum was cross-correlated with the future measurements to determine a shift in the SFAI spectrum. This shift shows the change in sound speed. The change in coefficient means it is 1-correlation coefficient. For each bacterium, two concentrations (colony forming units—CFU) were measured to show that the characteristics essentially remain the same.

Figure 7:
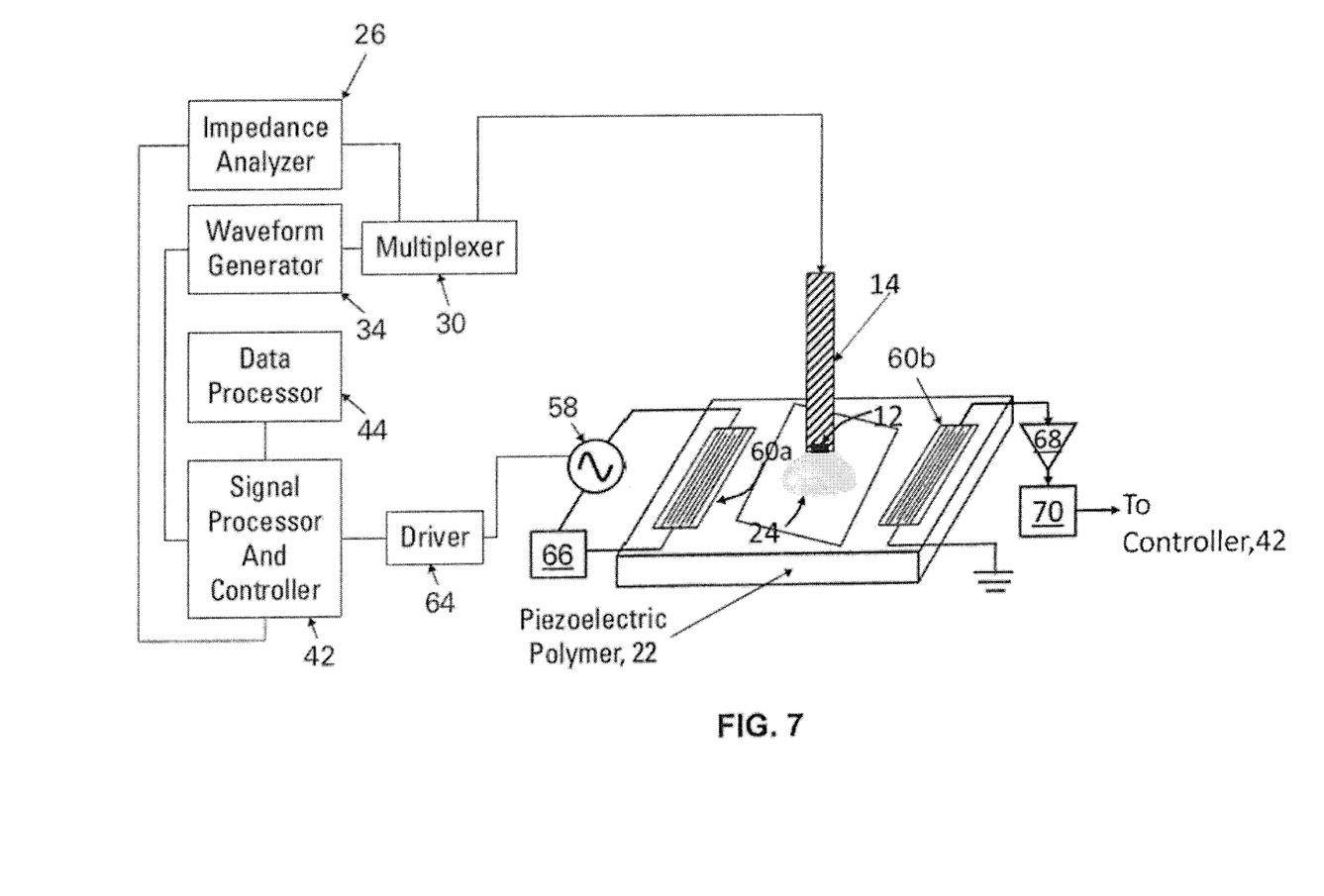
FIG. 7 is a schematic representation of a perspective view of another embodiment of an apparatus where an electric field is combined with acoustic measurements, illustrating generation of a Surface-Acoustic Wave (SAW) where the various molecules and polar materials interact with the surface charge that propagates on the surface of the substrate.

(ii) Another implementation is a combination of reflection mode SFAI and surface acoustic waves (SAW). Surface-acoustic waves (SAWs) are sound waves (Rayleigh or Love waves) that travel parallel to the surface of an elastic material, with their displacement amplitude decaying into the material such that they are confined to within roughly one wavelength of the surface. In a piezoelectric material such as gallium arsenide, quartz, or lithium niobate, the mechanical deformation associated with the SAW produces electric fields. The electric fields do not affect the propagation of the mechanical wave, so the result is a variation in electrostatic potential that travels along with the SAW. For use as a biosensor, the surface is coated with a biospecific layer corresponding to the analyte. The surface plays a major role since such a device depends on the mass change on the surface due to the attachments of various molecules and biomolecules that are detected by the frequency characteristics of the received signal by receiver IDT 60b. A change in a thin layer of the biomaterial is detected through the reflection mode SFAI, which relaxes the stringent requirement for specially treated surfaces for typical SAW device used as biosensor.

FIG. 7 illustrates an embodiment of a SAW device of the present invention, where the various molecules and polar material interact with the surface charge that propagates on the surface of the substrate. The SAW IDTs are shown as a pair, one operating as a transmitter, and the other as a receiver. However, for generating surface waves, a single IDT is required. Transmitter IDT 60a is driven by high-frequency sine-wave voltage source 58, controlled by driver 64 and controller 42 through impedance matching network, 66, while receiver IDT 60b directs an electrical signal to amplifier, 68, which amplified signal is received by digital signal processor, 70, and directed to controller, 42, and processor 44.

Another use for a SAW device is to concentrate fluorescent tagged material on the surface, thereby increasing the intensity of the fluorescence manifold in a regular (periodic) pattern that can be observed optically using a microscope placed below the lower, or second, side of the substrate. As an example, a simple 10×-500× digital microscope having USB output so that the image can be displayed or captured on the computer screen, may be used. The periodic pattern also affects the diffraction of the sound beam from the transducer in the reflection mode SFAI measurement, and can be monitored through the change in the sound reflection characteristics. The SAW devices operate at a much higher frequency than the SFAI system, and is particularly appropriate for liquid biopsy.

Figure 8A:
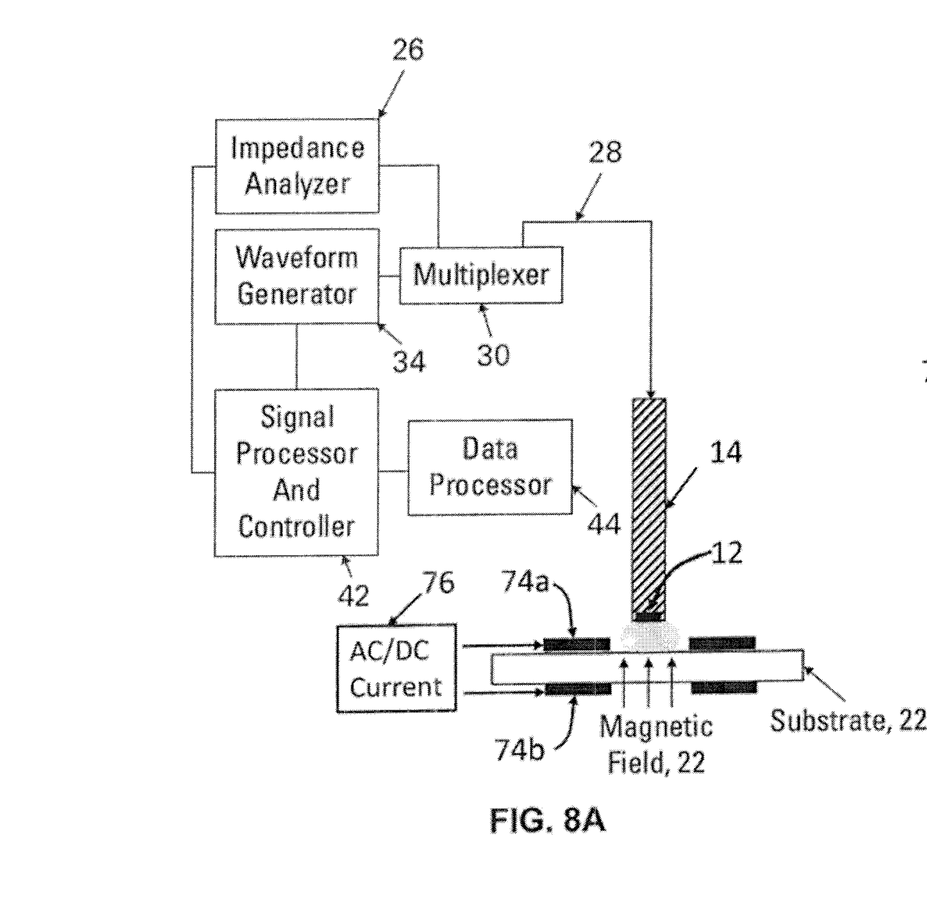

C. Combined Magnetic and Acoustic Measurements:
FIG. 8A, illustrates uniform magnetic field, 72, generated by placing two flat coils, 74a, 74b, on opposite side of substrate 22. Magnetic field 72 can be a DC field or a pulsed magnetic field depending on current source, 76. The reflective mode swept frequency acoustic interferometry apparatus is similar to that illustrated in FIG. 3, hereof. The two flat coils act as a Helmholtz coil to produce a uniform magnetic field perpendicular to the substrate surface. These coils are connected electrically in a manner that the magnetic fields produced by both are in the same direction. There are different types of coils that can be used and this is only an example. The coils are driven by an electric current that can be pulsed. The fluid drop is placed in the middle of the coil as shown and the piezoelectric transducer is placed on top of it. The rest of the functioning of the device is described in the setup as shown in FIGS. 3 and 5A. The acoustic part of the measurement is carried out in a slightly different way than before. For slow reacting systems where the time scale exceeds a few milliseconds, the measurement is done using frequency chirps of durations of a 10 μs-1 ms. The transducer is excited and the signal is detected and monitored over a few milliseconds to extract the multiple reflections of the signal in the fluid cavity formed between the substrate top surface and the crystal face. Once the received signal is processed, curves similar to those shown in FIG. 2D may be generated. The signal processing may be carried out using one of two procedures depending on the timescale involved. For very short timescales (1-100 μs), the processing includes cross-correlation of the excitation signal and the amplified received signal. However, more typical processing includes a frequency de-chirp process to determine time-of-flight. Both produce results similar to the curve illustrated in FIG. 2D.

For fast dynamics, where a continuous measurement is required, it is preferred to use a single frequency approach. Any arbitrary liquid resonance peak is selected as described in FIG. 2B and both its amplitude and phase are monitored by the electrical impedance of the liquid. Changes in magnetic orientation can be recorded as a function of time. For the above measurements, the observation begins when an electrical current signal is applied to the coils causing the fluid system to react and ultimately an equilibrium condition is established. The current is then switched off, and the decay of the system to the original randomized state of the magnetic moments is observed.

Magnetic biosensing relates to understanding the interactions between living systems and magnetic nanoparticles (MNPs). MNPs allow diagnosing the state and content of complex media both of non-organic and biological origin, with the assumption that the particles do not chemically react with the medium under study, thereby permitting specific "nondestructive testing". An advantage of magnetic nanosensors is that, with the aid of applied magnetic fields, analysis of remote motion excitation is possible.

Ferromagnetic nanoparticles, due to their small size, comprise single domains, thereby having constant magnitude magnetic moments. Such particles float in a water solution of macromolecules, some of which, possessing affinity to the particle surface are adsorb onto it, thereby transforming the particle environment from a Newtonian liquid into a viscoelastic polymer gel. In the absence of a magnetic field, Brownian motion randomizes directions of the magnetizations and the net magnetization of the ensemble is zero. However, if a uniform magnetic field is applied, the particle magnetic moments are oriented in the same direction. If this field is turned off quickly, the magnetic orientation decays back into the random behavior. There is a change in viscosity of the fluid due to this change, which can be ultrasonically detected using the reflection mode SFAI sensor. For example, the decay of the amplitude of subsequent echoes illustrated in FIG. 2D may be observed. This decay is due to the sound attenuation of the fluid, which is related to the viscosity of the fluid.

Magnetic beads (MBs) are a class of magnetic nanoparticles. In biosensing applications, these beads are largely composed of a magnetic core, a surface coating, and specific binding ligands at the surface of the beads. For the magnetic core material, iron oxides such as magnetite ($Fe_3O_4$) and maghemite ($\gamma$-$Fe_2O_3$) are considered to be attractive candidates for biological applications, because of their strong magnetic property and biocompatibility. Several ligands are available for the analytical purpose; antibodies (ABs), aptamers, and peptides. Aptamers are synthetic single-stranded (ss) DNA (deoxyribonucleic acid) or RNA (ribonucleic acid) molecules, which specifically bind to their target molecules with high affinity. Thus, aptamers serve as attractive bioreceptors. The orientation of the aptamer can readily be controlled during chemical synthesis, and various modifications can be made at defined positions within the aptamer sequence.

Figure 8B:
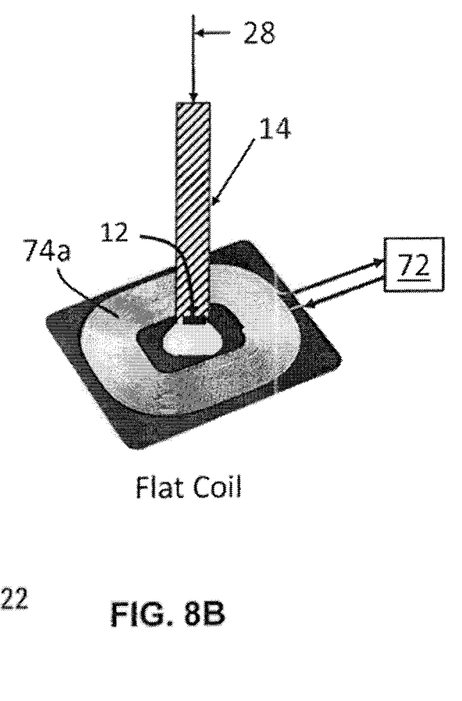
FIG. 8B is a schematic representation of a perspective top view of one of the two coils mounted on the substrate.

The MBs can be used to capture bacteria (e.g., *salmonella*), leukemia cells and various pathogens. The device shown in FIG. 8 can be used to detect the presence of pathogens and other biological entities. Appropriate functionalized MBs need to be added to the fluid and then a small quantity introduced into the device.

In addition to attenuation, it is also possible to monitor change in sound speed in a sensitive manner that can be as sensitive as 1 part $10^7$ with the present SFAI technique. This compares favorably to the QCM devices that are used for such detection through the change in mass of a thin layer of the material on a piezoelectric thin disc.

The magnetic state of blood varies based on its oxygenation level. There are other biomacromolecules that are affected by a magnetic field. The change in the fluid consisting of biomaterials is placed in this field is monitored by the reflection mode SFAI technique.

Another application utilizes the dynamic symmetry-breaking concept where the magnetic field is pulsed (e.g. a few cycles of a sine wave or any type of pulse), and is synchronized with the acoustic field. This is synchronized in a manner that the magnetic pulsed field is only excited during the half cycle of the sound field. The acoustic field is a pressure field that alternates between compression and rarefaction. The magnetic field is thus synchronized with all the compression part of the cycle or all the rarefaction part of the cycle. This is what is called symmetry breaking as the two halves of a cycle are no longer symmetric. So, if the cells are attached to magnetic nanoparticles coated with antibodies against a particular antigen, these can be rapidly separated. This combined separation is faster than acoustic separation alone. The SAW waves can also be used in this manner in combination with the periodic or pulsed magnetic field. In this situation, the separation is monitored by the acoustic probe. The separation can also be observed optically using a microscope.

D. Combined Optical, Electrical, Magnetic, and Acoustic Measurements:

Since the bottom surface of the substrate is free for optical observation at the same time, it is possible to combine photoacoustic and magnetic observations. Fast optical pulses that are absorbed by the fluid can raise the temperature of the fluid slightly and this affects the decay time as well. This allows probing of other physical properties of the fluid as well, such as specific heat, thermal diffusivity, etc. These types of simultaneous measurements are not available in any of the current standard measurement systems.

The coils need not be glued or attached to the system and there can be a small gap between the coil and the substrate. This allows placement of surface acoustic electrodes (IDTs) on the substrate (FIG. 7, and FIGS. 5B and 5C). Thus, simultaneous surface acoustic wave (SAW) stimulation and measurement are also possible. If the substrate is a piezoelectric material, the surface waves produce an oscillating electrical field on the substrate surface that can interact with the various functionalized magnetic beads and affect their magnetic moment orientations, thereby permitting the study of the complex interaction of both electric and magnetic fields at the same time. The SAW waves can be continuous or modulated in amplitude and frequency. Such combined effects cannot be studied through any existing biosensing instrument available today. Thus, embodiments of the present invention permit new diagnostic modalities for biosensing.

Optical excitation may be applied from below substrate 22, and magnetic coils may be disposed above and below substrate 22 may be added to the apparatus of FIG. 7, as described above. This permits a combination of optical, electrical, and magnetic fields to be used with reflective mode swept frequency acoustic interferometry to perform a variety of measurements. By placing transparent ITO electrodes on the substrate within the magnetic field region, it is possible to combine all four excitation fields. These fields may be independent or synchronized as required. Thus, embodiments of the present invention permit multimodal excitation of single drops of fluid and measurements to be made. Similar to the photoacoustic measurements described above, the acoustic sensor (the pinducer) may be used as a passive receiver such that the effects of pulsed magnetic, electric, or SAW excitations can be passively detected and monitored.

Embodiments of the present invention can be used for thin films, including tissue samples, or polymers, or almost any other material, as well as for droplets. Therefore, embodiments of the present apparatus can be adapted for many applications including observation of thin layers of materials on surfaces of various kinds, although not all modalities can used in all situations.

Embodiments of the present apparatus provide a general-purpose tool as a platform for making different types of measurements on small specimens using the same apparatus, which is not restricted to biomedical measurements. A laptop, a multichannel high-speed data-acquisition system, and a mechanical micrometer for adjustment are all that are needed to generate this low-cost measurement system. The ultimate goal is to be able to operate the apparatus with a smart phone or smart pad. The capability of performing the four major classes of blood tests: immunoassays, general chemistry assays, hematology assays, and assays that relied on the amplification of DNA in a faster and more simplified way by using the same platform device is now possible.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for optically and ultrasonically characterizing a single droplet of a liquid, comprising:
   a piezoelectric crystal effective for operating in a thickness longitudinal mode, and having an electrical impedance responsive to acoustic waves impinging thereon;
   a metal holder having a front surface having a cavity adapted to receive and hold, and electrically shield said piezoelectric crystal, said piezoelectric crystal forming a portion of the front surface of said metal holder;
   a flat, optically transparent substrate having a first surface and a second surface, the first surface being disposed parallel to and a chosen distance from the front surface of said metal holder, forming thereby an acoustic resonance cavity within which said single droplet is held by surface tension forces;
   a source of optical radiation for directing optical radiation onto the second surface of said substrate, through the first surface of said substrate, and into said single droplet;
   an electrical function generator for sweeping said piezoelectric crystal through a chosen frequency range, whereby a series of ultrasonic resonances, equally spaced in frequency, is generated in said single droplet;
   an electrical impedance analyzer for measuring the electrical impedance of said piezoelectric crystal as a function of frequency; and
   a signal processor for receiving an output from said electrical impedance analyzer and for determining a spacing between equally spaced ultrasonic resonances, from which speed of sound and sound attenuation in said single droplet are determined.

2. The apparatus of claim 1, further comprising a mechanical loading device for positioning the front surface of said metal holder in a vicinity of the first surface of said substrate onto which said single droplet has been placed.

3. The apparatus of claim 1, wherein said piezoelectric crystal can be swept between about 5 MHz and 20 MHz by said electrical function generator.

4. The apparatus of claim 1, wherein said optically transparent substrate comprises quartz.

5. The apparatus of claim 1, wherein said source of optical radiation comprises a tunable diode laser, or a high-power, multiple wavelength light emitting diode.

6. The apparatus of claim 5, wherein said source of optical radiation comprises a pulsed source of optical radiation.

7. Apparatus for electrically and ultrasonically characterizing a single droplet of a liquid, comprising:
   a piezoelectric crystal effective for operating in a thickness longitudinal mode, and having an electrical impedance responsive to acoustic waves impinging thereon;
   a metal holder having a front surface having a cavity adapted to receive and hold, and electrically shield said piezoelectric crystal, said piezoelectric crystal forming a portion of the front surface of said metal holder;
   a flat substrate having a first surface and a second surface, the first surface being disposed parallel to and a chosen distance from the front surface of said metal holder, forming thereby an acoustic resonance cavity within which said single droplet is held by surface tension forces, the first surface further having parallel or concentric electrically conducting portions thereon;
   an electrical function generator for sweeping said piezoelectric crystal through a chosen frequency range, whereby a series of ultrasonic resonances, equally spaced in frequency, is generated in said single droplet;
   an electric power supply for providing an electric field between the electrically conducting portions;
   an electrical impedance analyzer for measuring an electrical impedance of said piezoelectric crystal as a function of frequency; and
   a signal processor for receiving an output from said electrical impedance analyzer and for determining a spacing between equally spaced ultrasonic resonances, from which speed of sound and sound attenuation in said single droplet are determined.

8. The apparatus of claim 7, further comprising a mechanical loading device for positioning the front surface of said metal holder in a vicinity of the first surface of said substrate onto which said single droplet has been placed.

9. The apparatus of claim 7, wherein said piezoelectric crystal can be swept between about 5 MHz and 20 MHz by said electrical function generator.

10. The apparatus of claim 7, wherein said electric power supply comprises an ac electric power supply.

11. The apparatus of claim 7, wherein said electrically conducting portions comprise interdigitated electrically conducting portions.

12. Apparatus for magnetically and ultrasonically characterizing a single droplet of a liquid, comprising:
    a piezoelectric crystal effective for operating in a thickness longitudinal mode, and having an electrical impedance responsive to acoustic waves impinging thereon;
    a metal holder having a front surface having a cavity adapted to receive and hold, and electrically shield said piezoelectric crystal, said piezoelectric crystal forming a portion of the front surface of said metal holder;
    a flat substrate having a first surface and a second surface, the first surface being disposed parallel to and a chosen distance from the front surface of said metal holder, forming thereby an acoustic resonance cavity within which said single droplet is held by surface tension forces;
    an electrical function generator for sweeping said piezoelectric crystal through a chosen frequency range, whereby a series of ultrasonic resonances, equally spaced in frequency, is generated in said single droplet;
    two flat, parallel, spaced-apart coils, one of said two coils disposed on or in a vicinity of each of the first surface and the second surface of said substrate, and parallel thereto, each of said two coils having an axis collinear with an axis of the other of said two coils;
    a current source for providing electric current to each of said coils such that a uniform magnetic field perpendicular to the first surface and the second surface of said substrate is generated in the same direction by each coil;
    an electrical impedance analyzer for measuring an electrical impedance of said piezoelectric crystal as a function of frequency; and
    a signal processor for receiving an output from said electrical impedance analyzer and for determining a spacing between equally spaced ultrasonic resonances, from which speed of sound and sound attenuation in said single droplet are determined.

13. The apparatus of claim 12, further comprising a mechanical loading device for positioning the front surface of said metal holder in a vicinity of the first surface of said substrate onto which said single droplet has been placed.

14. The apparatus of claim 12, wherein said piezoelectric crystal can be swept between about 5 MHz and 20 MHz by said electrical function generator.

15. The apparatus of claim 12, wherein said current source is a pulsed current source.

16. Apparatus for electromagnetically and ultrasonically characterizing a single droplet of a liquid, comprising:
- a piezoelectric crystal effective for operating in a thickness longitudinal mode, and having an electrical impedance responsive to acoustic waves impinging thereon;
- a metal holder having a front surface having a cavity adapted to receive and hold, and electrically shield said piezoelectric crystal, said piezoelectric crystal forming a portion of the front surface of said metal holder;
- a flat substrate having a first surface and a second surface, the first surface being disposed parallel to and a chosen distance from the front surface of said metal holder, forming thereby an acoustic resonance cavity within which said single droplet is held by surface tension forces;
- an electrical function generator for sweeping said piezoelectric crystal through a chosen frequency range, whereby a series of ultrasonic resonances, equally spaced in frequency, is generated in said single droplet;
- a source of mm-wave electromagnetic radiation, said mm-wave electromagnetic radiation impinging on said single droplet;
- an electric power supply for providing power to said source of mm-wave electromagnetic radiation;
- an electrical impedance analyzer for measuring the electrical impedance of said piezoelectric crystal as a function of frequency; and
- a signal processor for receiving an output from said impedance analyzer and for determining a spacing between equally spaced ultrasonic resonances, from which speed of sound and sound attenuation in said single droplet are determined.

17. The apparatus of claim 16, further comprising a mechanical loading device for positioning the front surface of said metal holder in a vicinity of the first surface of said substrate onto which said single droplet has been placed.

18. The apparatus of claim 16, wherein said piezoelectric crystal can be swept between about 5 MHz and 20 MHz by said electrical function generator.

19. The apparatus of claim 16, wherein said source of mm-wave electromagnetic radiation generates frequencies between 30 GHz and 300 GHz.

20. The apparatus of claim 16, wherein said electric power supply is effective for tuning said source of mm-wave electromagnetic radiation over a chosen frequency range.

21. The apparatus of claim 16, further comprising a waveguide for directing said mm-wave electromagnetic radiation onto said single droplet.

\* \* \* \* \*